United States Patent [19]

Breiner

[11] Patent Number: 5,676,161
[45] Date of Patent: Oct. 14, 1997

[54] SURGICAL PROCEDURES FOR MASTOPEXY AND REDUCTION MAMMAPLASTY

[75] Inventor: Michael J. Breiner, Houston, Tex.

[73] Assignee: Baylor College of Medicine, Houston, Tex.

[21] Appl. No.: 427,754

[22] Filed: Apr. 24, 1995

[51] Int. Cl.$^6$ .................................................. A61B 19/00
[52] U.S. Cl. .................................................. 128/898
[58] Field of Search ........................... 128/897–98; 623/7

Primary Examiner—Angela D. Sykes
Assistant Examiner—John Lacyk
Attorney, Agent, or Firm—Bush, Riddle & Jackson

[57] ABSTRACT

A mastopexy or mammaplasty procedure to reshape and/or reduce the size of sagging breasts includes the steps of making a generally anchor-shaped incision having a bottom line along the inframammary crease, using a circular cutter to form the top portion of the incision and an incision around the areola to reduce the diameter thereof, after removing excess skin inside the incision, and breast tissue in the case of mammaplasty, shifting the areola, nipple and underlying breast tissue upward to position the areola/nipple complex within the circular top portion, pulling the flaps of skin formed to the sides of the incision down and around the areola and underneath same, and then suturing adjacent skin edges to complete the lifting and reshaping.

4 Claims, 1 Drawing Sheet

SURGICAL PROCEDURES FOR MASTOPEXY AND REDUCTION MAMMAPLASTY

FIELD OF THE INVENTION

This invention relates generally to a new and improved surgical procedure used in lifting the female breast and in reducing the size thereof, and particularly to procedures of the type described that uses a circular cutter in raising, recontouring and/or reducing sagging or enlarged breasts to improve an individual's appearance. The circular cutter is particularly useful in shaping the areola/nipple complex in such surgery.

BACKGROUND OF THE INVENTION

Sagging of the breasts, known as Ptosis, is a fairly common condition in older women, particularly older women who have had moderate to large breasts or whose breast tissues enlarged significantly during pregnancy and failed to return to their previous size. Sagging can also result from removal of a mammary implant. Where excess skin did not contract a bag of skin can be left which contains a disproportionally small amount of true breast tissue. As the skin brassiere was stretched, so was the areola which is that darker area of skin that surrounds the nipple. This stretching causes additional deformity. Many women consider sagging breasts and enlarged areolas to detract from their overall appearance, and desire to have a surgical procedure that improves the cosmetic or aesthetic appearance of the breasts. In patients with large breasts, surgical removal of the excess skin and breast tissue will not only improve appearance, but can alleviate back pain, shoulder strap marks and postural headache.

Since a mastopexy or a reduction mammaplasty typically involves surgical removal of excess skin and breast tissue and reduction in the size of the areola/nipple complex, the surgeon must use great care in locating and making incisions such that scars are as inconspicuous as possible, and so that both the breasts and the complexes are uniformly reshaped. In the past, all of the incisions were made essentially free-hand with a scalpel, and regardless of the skill of the surgeon a certain amount of non-uniformity could be expected. Of course absolute perfection is not obtainable in surgery of this type. However great improvements in appearance can be made using the procedures in accordance with this invention.

It is an object of the present invention to provide a new and improved mastopexy or reduction mammaplasty procedure that provides greatly improved appearance.

Another object of the present invention is to provide a new and improved mastopexy or reduction mammaplasty procedure where certain critical portions of the incisions are made with a circular cutter to provide substantially uniform reshaping and reduction.

SUMMARY OF THE INVENTION

These and other objects are obtained in accordance with the concepts of the present invention through the provision of a surgical procedure comprising the steps of making a generally anchor-shaped incision having its lower line curving along the inframammary crease beneath the breast, and upper lines that extend transversely from the respective outer ends of such lower line to points on either side and above the areola/nipple complex. The upper portion of the incision, which is above such complex, is shaped like a keyhole and has oppositely inclined incision lines on its sides that extend from the inner ends of the transverse incisions to a circular incision at the top that is vertically aligned with the complex. A circular cutter is used to make such top incision as well as the same diameter incision around the areola which gives the annular area of darker skin a lesser outer diameter. The conventional scalpel is used to make all other parts of the incision. The excess skin and the outer portion of the areola within the boundaries of the incision are removed, and then the nipple, the reduced areola and the underlying breast tissue are shifted upward to a higher location where the areola/nipple complex is located in the circular top portion of the keyhole-shaped incision. Then the flaps of skin that formerly were above and to the sides of the complex are brought down, around and together underneath the new location thereof to reshape the breast. The adjacent skin edges under the breast, the inner sides of the flaps, and the circular edges around the new or reduced diameter nipple-areola complex are sutured to complete the breast reshaping process. These same steps are used in the reduction mammaplasty except that excess breast tissue is removed or resected before lifting and relocation of the nipple/areola complex.

BRIEF DESCRIPTION OF THE DRAWINGS

The present invention has the above as well as other objects, features and advantages which will become more clearly apparent in connection with the following detailed description of a preferred embodiment, takes in conjunction with the appended drawings in which.

DETAILED DESCRIPTION OF A PREFERRED EMBODIMENT

Figure 1:
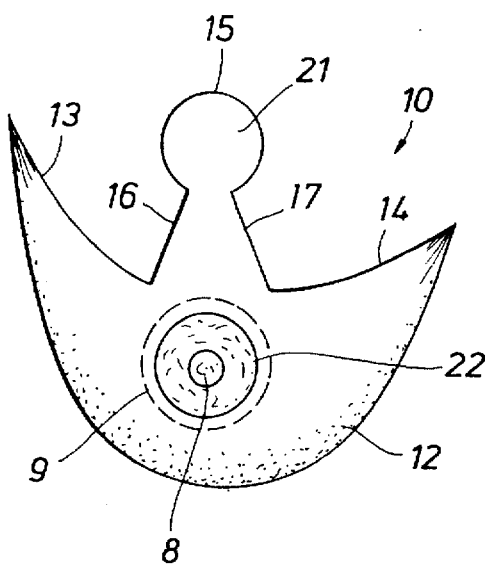
FIG. 1 shows a sagging breast with incision lines marked thereon to outline the skin removal area.

Referring initially to FIG. 1, the number 10 indicates generally a breast that has sagged for any of the various reasons noted above, and which is to be reshaped or reduced and reshaped in accordance with this invention. Of course the breast 10 has an areola 9 and a nipple 8, the perimeter of the areola being depicted by a phantom line after radial stretching for the various reasons set forth above. In effect, the mastopexy procedure fashions a properly fitting brassiere with the patient's own tissue. To this end, a pattern of lines is drawn on the patient in the sitting position immediately prior to the surgical procedure. This pattern includes a curved lower line 12 that follows the inframammary crease beneath the breast 10, transverse lines 13, 14 which extend inward from the respective outer ends of the line 12, and a keyhole-shaped subpattern above the areola 9 and the nipple 8. The keyhole subpattern has a circular top line 15 and straight side lines 16, 17 which incline downward and outward to meet the respective inner ends of the transverse lines 13, 14. Of course the same pattern of lines is marked on the other breast of the patient. Then the patient is placed under general anesthesia, although local anesthesia to numb the area around the breasts may be used.

Figure 2:
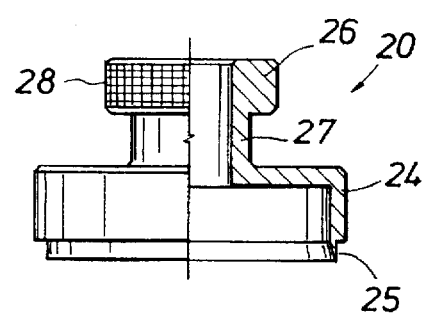
FIG. 2 shows a circular cutter for making certain portions of incisions shown in FIG. 1.

A circular cutter 20 as shown in FIG. 2 is used to make the incision around the circular area 21 bounded by the top line 15, and to make the same diameter incision 22 in the areola 9. In most cases the incision 22 around the nipple-areola complex 8, 9 will define a circular area having a somewhat lesser diameter than the areola had before because this complex almost always is stretched as a part of the sagging process, for example out to the circumference shown in phantom line in FIG. 1. The cutter 20, which can be made in various diameters, has a circular lower portion 24 in the shape of an inverted cup, such portion having a sharp bottom edge 25. A reduced diameter upper portion 26 is joined to the lower portion 24 by a hollow stem 27. The upper portion 26 is knurled at 28 to improve gripping. The surgeon holds the upper portion 26 between the thumb and index finger and centers the cutting edge 25 on the site to be incised. Then while holding downward pressure, the cutter 20 is gently rotated somewhat to cause the edge 25 to cut through the skin. When the cutter 20 is removed a perfectly round incision will have been made that is impossible to duplicate with a hand-held scalpel. After the circular incisions 15 and 22 have been made with the cutter 20, all other incisions are made with a scalpel along each of the lines 12-14, 16 and 17. The excess skin in the area shown in dash-dot-dash lines in FIG. 3 then is removed in an appropriate manner.

Figure 3:
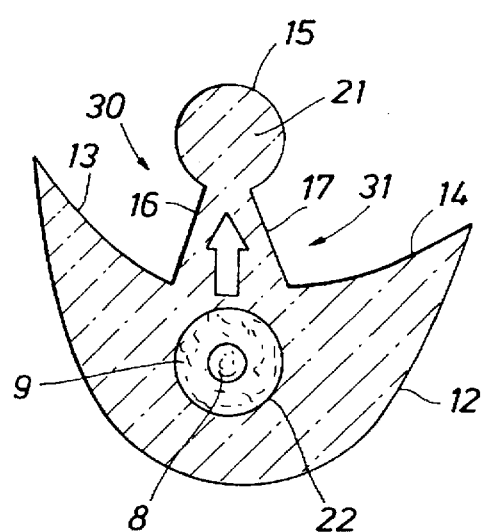
FIGS. 3 and 4 shows tissue relocation and skin repositioning.
Figure 4:
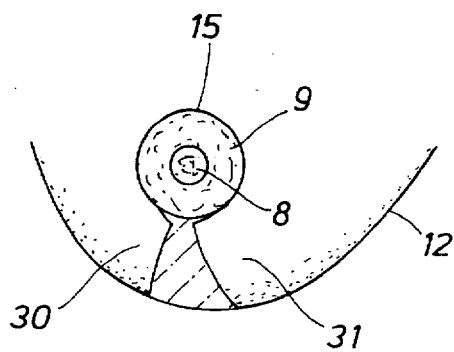
Figure 5:
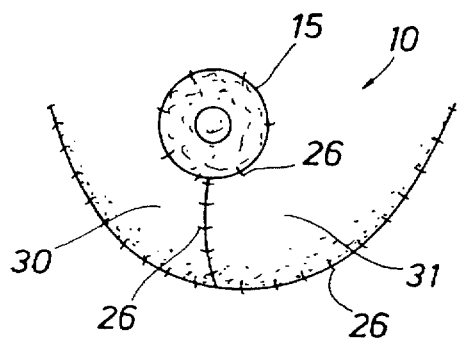
FIG. 5 shows the reshaped breast with sutures closing all the incisions.

To reshape the breast in a mastopexy, the nipple 8, the surrounding areola 9 and the underlying breast tissue are moved or shifted upward as shown by the large arrow in FIG. 3 to a higher location where the areola is centered in the area 21 bounded by the line 15. Then the flaps of skin 30, 31 are brought down, around and toward one another underneath the areola 9 to reshape the breast 10 as shown in FIG. 4. Sutures 26 then are used to close all wounds under the breast 10 and around the areola 9 as shown in FIG. 5. The procedure then is complete and provides higher, well contoured breasts where incision scars are all below and around the nipples and thus not noticeable even in low cut clothing.

The same incision procedure is used for a reduction mammaplasty except that a desired amount of breast tissue is removed before lifting and repositioning the remaining tissue.

Under some circumstances the mastopexy procedure disclosed herein can be combined with the use of a small implant to augment the size of the breasts 10. The prosthesis is positioned in a pocket created either directly under the breast tissue, or underneath the chest wall muscle. A typical prosthesis is a flexible plastic envelope that contains a silicone gel, saline solution or a combination of these materials.

It now will be apparent that a new and improved surgical procedure has been disclosed which lifts saggy, loose breasts, particularly breasts that have lost volume and elasticity after childbearing. The procedure also is applicable to breast reductions. The diameter of the areola can be reduced in the same procedure. Greater precision and uniformity is obtained through the use of a circular cutter in repositioning the new areola as disclosed herein. Since certain changes or modifications may be made in the disclosed embodiment without departing from the inventive concepts involved, it is the aim of the appended claims to cover all such changes and modifications falling within the true spirit and scope of the present invention.

What is claimed is:

1. A surgical procedure to lift and reshape or reduce sagging breasts, comprising the steps of: making a generally anchor-shaped incision having a curved lower line which follows the inframammary cease beneath the breast and terminates upwardly at ends on opposed sides of the breast, transverse lines extending inwardly from the respective ends of said curved lower line to inner ends located above the areola, and an upper portion having lines shaped generally like a keyhole located above the areola including a circular upper line and spaced apart side lines that extend down from said circular upper line to the inner ends of said transverse lines to define a flap of skin on each side of said upper portion; incising said circular upper line using a circular cutter and making a circular incision around said areola which reduces the diameter thereof; removing any excess skin and areola outlined by said incision; shifting the nipple, areola and underlying breast tissue upward until the reduced diameter areola is repositioned within said circular upper incision line; pulling said flaps of skin down and around said areola and underneath same; and then suturing all adjacent skins edges to complete the reshaping of said breast.

2. The procedure of claim 1 wherein said circular upper incision line and the circular incision around said areola have substantially the same diameter.

3. The procedure of claim 1 where said spaced apart lines each incline downward and outward relative to one another.

4. The procedure of claim 1 including the additional step of removing a selected amount of tissue from the breast to reduce the size thereof before carrying out said shifting step.

* * * * *